United States Patent [19]

Naumann et al.

[11] 4,243,554
[45] Jan. 6, 1981

[54] MOLYBDENUM DISULFIDE CATALYST AND THE PREPARATION THEREOF

[75] Inventors: Alfred W. Naumann, Charleston, W. Va.; Albert S. Behan, Bronxville, N.Y.

[73] Assignee: Union Carbide Corporation, New York, N.Y.

[21] Appl. No.: 47,239

[22] Filed: Jun. 11, 1979

[51] Int. Cl.³ .................. B01J 27/02; B01J 27/24; C01G 37/00
[52] U.S. Cl. .................. 252/439; 252/438; 423/53
[58] Field of Search ............ 252/438, 439; 423/53

[56] References Cited

U.S. PATENT DOCUMENTS

| | | | |
|---|---|---|---|
| 2,112,292 | 3/1938 | Jones | 423/53 X |
| 2,367,946 | 1/1945 | Koercher | 423/53 |
| 2,490,488 | 12/1949 | Stewart | 260/449.6 |
| 2,686,763 | 8/1954 | Johnson et al. | 252/439 X |
| 3,156,420 | 11/1964 | Crowl | 252/25 X |
| 3,390,080 | 6/1968 | Groszek | 252/25 |
| 3,876,755 | 10/1973 | Kurtak et al. | 423/56 |
| 4,098,839 | 7/1978 | Wilms et al. | 252/439 X |
| 4,151,191 | 4/1979 | Hoppel et al. | 252/439 X |

FOREIGN PATENT DOCUMENTS

| | | | |
|---|---|---|---|
| 1473900 | 3/1967 | France | 252/439 |
| 7603197 | 3/1976 | Netherlands | 252/439 |

OTHER PUBLICATIONS

Sulphide Catalysts their Properties and Applications, Otto Weisse and Staneslas Landa. Pergamon Press, 1973, p. 57, Printed in Czechoslovokia.
"Thermal Decomp. of $(NH_4)_2MoO_2S_2$", T. P. Prasad et al., J. of Inorg. Nucl. Chem., 1973, vol. 35, pp. 1895-1904.
Mills & Steffgen, Cat. Rev. 8,159, (1973).
Noble Metals, Mo. & W in Hydrocarbon Synthesis Shultz, et al., Jul., 1967, Bu. of Mines Report 6974.
Angew, Chem. Int. Ed. Engl. 17, 535, (1978).
Angew, Chem. Int. Ed. Engl. 17, 279, (1978).

Primary Examiner—Delbert E. Gantz
Assistant Examiner—William G. Wright
Attorney, Agent, or Firm—Harrie M. Humphreys

[57] ABSTRACT

High surface area molybdenum disulfide, $MoS_2$, is produced by the thermal decomposition of selected ammonium thiomolybdate salts at temperatures of about 300°–800° C., with said salts being heated to decomposition temperature at a rate in excess of about 15° C./min., e.g., about 20°–30° C./min., in an essentially oxygen-free atmosphere. The product molybdenum disulfide has superior catalytic properties for the water gas shift and methanation reactions compared with conventional $MoS_2$. The stability of the catalyst is enhanced by decomposing the thiomolybdate salt in admixture with an inert, preformed particulate diluent or by bulk doping said salt with tungsten or vanadium prior to decomposition of the salt. The molybdenum disulfide of the invention also has desirable properties for use in catalyzed hydrogenation and hydrotreating reactions, i.e., hydrodenitrogenation and hydrodesulfurization reactions, particularly when employed in nickel or cobalt-promoted form.

24 Claims, No Drawings

MOLYBDENUM DISULFIDE CATALYST AND THE PREPARATION THEREOF

BACKGROUND OF THE INVENTION

1. Field of the Invention

The invention relates to molybdenum disulfide catalysts. More particularly, it relates to the preparation of such catalysts having enhanced catalytic properties.

2. Description of the Prior Art

The catalytic hydrogenation of carbon monoxide to form methane is a well known, established methanation reaction. This reaction:

$$CO + 3H_2 \rightarrow CH_4 + H_2O, \quad (1)$$

utilizes a synthesis gas, as from the gasification of coal with oxygen and steam. Prior to methanation, the gas stream is commonly treated to provide a desired $H_2/CO$ ratio and to remove excess $CO_2$ and deleterious impurities such as sulfur impurities. As the $H_2/CO$ ratio of the raw synthesis gas is generally substantially below the necessary minimum ratio of 3/1, at least a portion of the carbon monoxide is generally first reacted with steam, over an iron or other suitable catalyst in the well-known "water gas shift" reaction as follows:

$$CO + H_2O \rightarrow CO_2 + H_2. \quad (2)$$

Excessive $CO_2$ in the gas stream is removed by conventional means, such as by treatment with alkaline absorbents. Sulfur impurities are also removed to substantially under 5 ppm, e.g. to less than about 1 ppm, preferably to less than 0.2 ppm, to protect the methanation catalyst from poisoning by such sulfur impurities. Hydrogen sulfide or other sulfur bearing gases are absorbed, selectively or non-selectively, by the absorbent employed for carbon dioxide removal. When necessary, final cleanup may be accomplished by passing the gas stream through iron oxide, zinc oxide or activated carbon to remove residual traces of $H_2S$ or organic sulfides.

In view of the diminishing supply of natural gas, such methanation techniques are of considerable interest in the art as a means for producing substitute natural gas (SNG) from coal, shale oil, tar sands, petroleum residues, biomass, industrial and municipal waste, and other complex carbonaceous material. While a variety of specific processing techniques for SNG production have been proposed in the art, essentially all of these techniques provide for the steps of (1) gasification, to produce crude mixtures of CO, $H_2$, $CO_2$, $H_2O$, $CH_4$ and other trace components; (2) catalytic water gas shift to adjust the $CO:H_2$ ratio as indicated above; (3) and catalytic methanation in accordance with reaction (1) above and related reactions that might occur, such as:

$$CO_2 + 4H_2 \rightarrow CH_4 + 2H_2O \text{ and/or} \quad (3)$$

$$2CO + 2H_2 \rightarrow CH_4 + CO_2. \quad (4)$$

The methanation catalysts currently being seriously considered for commercialization are based on nickel or cobalt as the active ingredient. These metallic catalysts are very active, selective and relatively cheap. They are, however, extremely sensitive to poisoning by sulfur compounds. Since almost all of the carbonaceous feeds employed for synthesis gas production contain sulfur that is converted largely to $H_2S$ during the initial gasification step, costly acid gas purification operations must be included in SNG process designs so as to lower the $H_2S$ level to the fractional ppm level indicated above to achieve commercially feasible, long catalyst life. It would be highly desirable in the art, therefore, if sulfur-resistant methanation catalysts were commercially available as this would permit a considerable reduction in the degree of gas purification processing required prior to the methanation step in SNG production operations. If such a catalyst would also catalyze water shift reaction (2) effectively, the number of individual processing steps, and the overall cost of SNG production could be even further reduced.

It has long been recognized in the art that molybdenum sulfide, $MoS_2$, and tungsten sulfide, $WS_2$, as well as more complex mixed sulfides, are sulfur-tolerant methanation catalysts. $MoS_2$ occurs native as molybdenite and can be prepared artifically by heating molybdenum dioxide, molybdenum trioxide or ammonium molybdate in $H_2S$ or sulfur vapor. Thus, Mills and Steffgen, in Catalyst Rev. 8, 159 (1973), review the results of several studies with molybdenum and tungsten sulfide methanation catalysts prepared in a variety of ways. Even the best of these catalysts were only moderately active. In the Stewart patent, U.S. Pat. No. 2,490,488, $MoS_2$ catalysts modified by the addition of alkali metal compounds are disclosed as shifting the hydrocarbon synthesis of synthesis gas from methane to a mixture of higher molecular weight products. A CO conversion of 95% was achieved at 280° C. and 200 psig, at a commercially impractical space velocity (SV) of 86 $hr^{-1}$. A temperature of 410° C. was required to achieve 98% conversion at an SV of 100 $hr^{-1}$.

Methanation activity for molybdenum catalysts, including those prepared as sulfides, was reported by Schultz et al, U.S. Bureau of Mines, Rep. Invest. No. 6974 (1967). In the preparation of catalyst L 6135, $H_2S$ gas and an aqueous solution of aluminum nitrate were added to an ammoniacal aqueous solution of ammonium molybdate to precipitate a mixture of ammonium thiomolybdate and hydrated aluminum hydroxide. This coprecipitate was reduced in $H_2$ before use. When employed with a stream having a $CO:H_2$ ratio of 1:3 at 400° C., the CO conversion was 47.6% at a space velocity of only 295 $hr^{-1}$. Shultz et al also prepared catalysts by impregnating silica-alumina or activated carbon supports with ammonium molybdate, followed by calcining, to give a supported molybdenum oxide for which a conversion of 76.6% was reported at 420° C. and 21 atm. This catalyst was not sulfided. Other catalysts prepared as oxides by coprecipitating aluminum and molybdate salts, without sulfiding, provided methanation performance similar to that of impregnated materials.

Such previously available molybdenum methanation catalysts, including $MoS_2$ catalyst materials, are relatively inactive, and are not generally considered to possess sufficient activity to justify use in commercial operations. Despite the desirable sulfur resistant properties of $MoS_2$ materials, therefore, such available materials have not been suitable for practical use in providing synthetic natural gas to meet existing and anticipated requirements for low-cost, high BTU gaseous heating fuels.

There remains a need in the art, therefore, for an improved methanation catalyst having an acceptable degree of activity for use in commercial operations, coupled with an absence of the extreme sensitivity to poisoning by sulfur compounds that is characteristic of the active nickel and cobalt catalyst compositions. The satisfactory catalytic activity and the reduced acid gas purification requirements thus achieved would enable the overall SNG production operations to be carried out in a manner enhancing, on an overall technical-economic basis, the production of low-cost, high purity SNG as a replacement for natural gas.

It is an object of the invention, therefore, to provide an improved, sulfur-resistant methanation catalyst.

It is another object of the invention to provide a sulfur-resistant molybdenum disulfide catalyst of improved catalytic activity.

It is another object of the invention to provide an improved molybdenum disulfide catalyst capable of enhancing the overall operation for the production of SNG.

With these and other objects in mind, the invention is hereinafter disclosed in detail, the novel features thereof being particularly pointed out in the appended claims.

SUMMARY OF THE INVENTION

High surface area molybdenum disulfide is produced by thermally decomposing various ammonium thiomolybdate salts, such as an ammonium salt of a molybdenumsulfur cluster anion, or an ammonium thiomolybdate salt having the formula $(NH_4)_2$ $[MoO_xS_{4-x}]$, as where x is 2. Decomposition is carried out at temperatures of about 300°–800° C., preferably about 400°–500° C., with the thiomolybdate salt being heated to the decomposition temperature rapidly at a rate in excess of 15° C./min. in an essentially oxygen-free atmosphere. The thiomolybdate salt can be decomposed in admixture with an inert, preformed particulate diluent or can be bulk-doped with tungsten or vanadium prior to decomposition, with the resulting catalyst material obtained upon decomposition having enhanced stability characteristics. The $MoS_2$ can be employed as a water gas shift and/or methanation catalyst and is advantageous for use, particularly in nickel or cobalt promoted form, for catalyzing hydrogenation or hydrotreating reactions.

DETAILED DESCRIPTION OF THE INVENION

The objects of the invention are accomplished by a novel process for the preparation of molybdenum disulfide, $MoS_2$, having desirable properties for use as a methanation catalyst in addition to the sulfur resistant characteristics commonly associated with molybdenum disulfide. Previously available $MoS_2$, as indicated above, does not have sufficient activity to warrant its consideration, on an overall technical and economic basis, as a methanation catalyst, in commercially feasible SNG operations.

The present invention relates to the thermal decomposition of a selected ammonium thiomolybdate salt under specific decompositon conditions to produce a $MoS_2$ catalyst material having desirable properties for water gas shift, methanation, hydrogenation, hydrotreating and like catalyst applications. In some embodiments of the invention, the thiomolybdate salt comprises an ammonium salt of a molybdenum-sulfur cluster anion. An example of such a salt, and a generally preferred salt for use in the practice of the invention is the crystalline compound $(NH_4)_2[Mo_3S(S_2)_6] \cdot x\ H_2O$ as disclosed in Angew. Chem. Int. Ed. Engl. 17, 535 (1978), said compound being referred to herein as APTM. Said reference indicates that the existence of the homologous $(NH_4)_4$ $[Mo_4S_4\ (S_2)_4]$ could be predicted. Another such cluster compound that can be used in the practice of the invention is $(NH_4)_2$ $[Mo_2(S_2)_6]$ reported by Muller, et al., Angew. Chem. Int. Ed. Engl. 17, 279 (1978). The ammonium thiomolybdate salts include those having the formula $(NH_4)_2[MoO_xS_{4-x}]$, as where x is 0 or 2, with an x of 2, i.e., ammonium oxythiomolybdate (AOTM), being preferred. It will be understood by those skilled in the art that the ammonium salts of various other molybdenum-sulfur cluster anions may exist and constitute suitable starting materials for the invention, it being appreciated, however, that not all such materials that may be or become available in the art will be suitable or desirable for practical use as a starting material in the $MoS_2$ process of the present invention. Likewise, it will be understood that a mixture of such ammonium thiomolybdate salts may actually be employed so that x may actually range from about 0.8 to about 2.2 within the scope of the invention.

Thermal decomposition of ammonium thiomolybdate salts have been reported in the J. Inorg. Nucl. Chemistry, 35, 1895-1904 (1973), with the thermal decomposition of $(NH_4)_2\ MoO_2S_2, (NH_4)_2\ MoS_4, (NH_4)_2\ WO_2S_2$ and $(NH_4)_2\ WS_4$, being disclosed, in accordance with available analytical techniques using a Mettler instrument and a DTA/TGA instrument of Linseis KG, West Germany. The experiments were carried out under nitrogen atmosphere at normal pressure employing a heating rate of 6° C./Min., a heating rate of 6°–10° C./min. being conventional for such analytical procedures. At a decomposition temperature of 400° C., $MoS_2$ was reported as the probable composition. Such analytical procedures did not, however, relate to the potential advantages and disadvantages of $MoS_2$ as a methanation catalyst.

The invention herein disclosed and claimed, on the other hand, is directed to a process for producing a novel $MoS_2$ catalyst product having commercial application by the thermal decomposition of selected ammonium thiomolybdate salts under controlled conditions. As a result, a form of bulk, high surface area molybdenum disulfide is formed that has superior catalytic properties for the water gas shift, methanation and other catalytic reactions compared with previously described $MoS_2$ catalysts prepared by previously known methods.

The thiomolybdate salts are decomposed, in the practice of the invention, at a decomposition temperature of from about 300° C. to about 800° C., preferably at a temperature of from about 400° C. to about 500° C. Contrary to the standard heating rate of 6°–10° C./min. for the conventional analytical decomposition technique referred to above, it has been found that an $MoS_2$ having improved catalytic properties is obtained by decomposing the various indicated ammonium thiomolybdate salts, conveniently in the form of small pressed pellets rather than loose powder, very rapidly at a rate in excess of about 15° C./min. While it is generally preferred to employ heating rates within the range of from about 20° C./min. to about 30° C./min., it will be understood that even more rapid heating rates may be employed, as by preheating the decomposition zone to the desired preheat temperature prior to the introduction of the ammonium thiomolybdate salt into said zone. By carrying out the preheating of the indicated salts at the rapid rates herein disclosed, the $MoS_2$ product is found to have the desirable catalytic properties indicated above, whereas heating the same salts at conventional rates does not result in such beneficial results to the same desirable extent.

The required rapid rate of heating is accomplished in an essentially oxygen-free atmosphere. For this purpose, decomposition can be conveniently carried out in a nitrogen or argon atmosphere or under vacuum. It is within the scope of the invention to have hydrogen present in said essentially oxygen-free atmosphere. The hydrogen content may range from 0 to 100% by volume based on the total volume of essentially oxygen-free atmosphere in the decomposition kiln or other decomposition zone employed. Such hydrogen will ordinarily be present in amounts up to about 10% by volume of hydrogen in the overall nitrogen or argon atmosphere. Forming gas may conveniently be employed as the essentially oxygen-free atmosphere.

Upon carrying out the decomposition of selected thiomolybdate salts under such decomposition conditions for a sufficient time to permit decomposition of the salts, the product molybdenum disulfide is obtained as a high surface area, bulk form of material having desirable catalytic properties. The $MoS_2$ product will thus have a surface area of from about 50 to about 150 m$^2$/gm. It should be noted, however, that the high surface area is a factor, but only one factor, in the improved catalytic properties resulting from the production of $MoS_2$ in accordance with the present invention. The improved properties result, to the contrary, from the particular decomposition conditions employed with the selected ammonium thiomolybdate salts disclosed herein. Such conditions result in the production of an active $MoS_2$ catalytic product that is obtained in said bulk, high surface area form. The decomposition conditions of the invention do not result in improved catalytic properties for all thiomolybdate salts, however, but unexpectedly achieve such results with those herein disclosed as falling within the scope of the invention.

For purposes of trials under the invention, APTM, i.e., $(NH_4)_2 Mo_3S_{13} \cdot x H_2O$, where x is generally from 0 to 2, was prepared by the procedure of the Kurtak, et al., patent, U.S. 3,876,755 in which the subject APTM material was described as having the empirical formula 3 $MoS_4 \cdot 2NH_4OH$.

In the preparation of ammonium thiomolybdate salts, ammonium thiomolybdate, $(NH_4)_2 MoS_4$, i.e. ATM, was prepared as follows. A solution of 200 g ammonium paramolybdate, 200 ml reagent ammonium hydroxide, and 1 l water was cooled to about 5° C. in an ice bath. With the reaction flask still in the bath, gaseous hydrogen sulfide was introduced at a slightly higher rate than could be absorbed by the solution. The hydrogen sulfide flow was monitored by venting the flask to a water bubbler through which a slow but steady bubble rate was monitored. As the hydrogen sulfide was introduced, the temperature of the mixture increased to 50°–60° C. The flow of hydrogen sulfide was continued until there was no observable further consumption, and the temperature had returned to 20°–30° C. The deep red ATM precipitate formed by this treatment was collected by filtration, washed with denatured alcohol, and dried in air at room temperature.

The procedure for AOTM, ammonium oxythiomolybdate, $(NH_4)_2 MoO_2S_2$, was similar, except that temperatures were lower, and less hydrogen sulfide was added. The reaction mixture was cooled to about 1° C., and maintained below 10° C. thereafter. Hydrogen sulfide was added until a yellow precipitate (AOTM) formed, then continued another 20 minutes before filtering and washing. The precipitate was dried under vacuum to prevent a darkening that might otherwise occur if the material is dried in air.

Unless otherwise noted, the thiomolybdate salts used in the trials herein reported were converted to $MoS_2$ products, or doped variations thereof, by heating said salts rapidly to 400°–500° C. in nitrogen or 10% H$_2$/argon, taking about ½ hour or less to reach decomposition temperature, i.e. heating at about 15° C./min. or more. The salts were held at decomposition temperature for 1–3 hours, then cooled to room temperature either under nitrogen or H$_2$/argon. Air was introduced gradually at room temperature by incremental increases in air concentration of an air/nitrogen mixture. The $MoS_2$ thus produced was pelletized for catalytic evaluation by either pressing into ⅛" diameter ×⅛" long cylinders, or by forming ½" diameter ×¾" cylinders that were subsequently crushed and sized to 10/20 mesh.

Catalysts prepared in accordance with the invention have been evaluated in a tubular reactor under varying conditions of temperature, pressure, CO:H$_2$ ratio and gas hourly space velocity (SV, in hr.$^{-1}$). Conditions of 400° C. outlet temperature, 400 psig, CO:H$_2$ ratios of 1:3 and SV of 3300 hr$^{-1}$ were most commonly employed. The advantages of the invention were demonstrated by comparing performance data obtained by means of $MoS_2$ prepared in accordance with the invention with $MoS_2$ prepared by methods believed representative of the prior art teachings as indicated above. The reactor employed was a one cm. I.D. reactor containing approximately 15 ml., typically about 20 grams, of catalyst, a back-pressure regulator that maintained the system at a preset constant pressure, a differential flow controller-needle valve combination that maintained a constant flow into the system, and an on-line gas chromatograph and wet test meter to monitor the composition and volume of the product stream. The reactor was mounted vertically in an 8" Lindberg clamshell furnace having a 1" bore. The temperature of the reactor was maintained with a West SCR Stepless Controller via a thermocouple attached to the outside of the reactor. Catalyst temperature was measured by a second thermocouple mounted axially in the reactor with the tip about one cm. from the bottom of the bed. The sulfide catalysts were significantly more active for the water gas shift reaction, i.e. reaction (2), than for methanation, i.e. reaction (1). Reflecting this, two measures of catalyst performance were used for evaluation purposes. These were (a) the percent of the CO fed to the system that was converted to hydrocarbons, e.g. methane, ethane, propane, and (b) total CO conversion, i.e. the amount of CO converted to hydrocarbons plus the amount consumed by the shift reaction. Surface areas were determined by a single point BET method using a Quantachrom Monosorb Analyzer. The catalytic performance of the various $MoS_2$ types is summarized in the Table below:

TABLE

| | | Catalytic Performance | | | |
|---|---|---|---|---|---|
| | | Initial(a) Performance | | After Overnight Operation | |
| | Catalyst Type | % CO to Hydrocarbons | % CO Conv. | % CO to Hydrocarbons | % CO Conv. |
| 1. | Commercial $MoS_2$ | nil | nil | — | — |
| 2. | Sulfided Ammonium Paramolydbate (APM) | 36 | 63 | — | — |
| 3. | Sulfided $MoO_3/Al_2O_3$ | 48 | 82 | — | — |
| 4. | Sulfided Climax Mo-$MoO_2$ | 30 | 54 | — | — |
| 5. | $MoS_2$ from Ammonium Thiomolybdate (ATM) | 75 | 99 | 63 | 90 |
| 6. | $MoS_2$ from Ammonium Oxythiomolybdate (AOTM) | 81 | 799 | 81 | 799 |
| 7. | $MoS_2$ from the Ammonium salt of Molybdenum-Sulfur Cluster Anion (APTM) | 87 | 799 | 82 | 799 |

(a) 400° C. outlet; 400 psig; $CO:H_2 = 1:3$; SV = 3000 hr$^{-1}$
$^b$ obtained from American Metals Climax Co.

As can be seen from the results both for total CO conversion, i.e., water gas shift plus methanation, and the conversion of CO to hydrocarbons, i.e., methane plus smaller amounts of higher paraffins, in the Table, the state-of-the-art catalysts, i.e., catalysts 1-4, were markedly inferior to the $MoS_2$ catalysts of the invention, i.e., catalysts 5, 6 and 7, prepared by decomposition of thiosalts in accordance with the decomposition process herein disclosed in claimed. As will be appreciated from the results set forth, the $MoS_2$ catalyst prepared from ammonium thiomolybdate (ATM), catalyst 5, represents a significant improvement over conventional molybdenum sulfide catalysts 1-4 but is significantly less efficient than catalysts 6 and 7.

In the practice of the invention, various modifications can be employed to enhance the stability of the catalyst. Such modifications include decomposing the thiomolybdate salt in admixture with an inert, preformed particulate diluent, bulk doping the thiomolybdate salt, as with tungsten or vanadium, prior to decomposition, or mixing the catalyst product with a suitable catalyst support additive for desired support and/or dispersion of the active catalyst material. Each of these modifications is discussed below as means to extend catalyst life by retarding the effects of sintering that leads to a decrease in the amount of exposed catalyst surface, which, in turn, leads to a decrease in catalytic activity.

As is known in the art, sintering, with resultant decline in catalytic activity, can be retarded by mixing or matrixing the catalyst with particles of a phase with which it is inert. When properly compounded, the particles of the second phase serve as spacers to keep the catalyst particles separated, reducing greatly the number of contacts between catalyst particles and the opportunities for sintering or coalescence. It has also been common practice to disperse precious metal catalysts as isolated, very small particles on a catalyst support. Bulk or surface doping with appropriate additives can also be employed to retard sintering and prolong catalyst life.

Improvement in the long-term stability of the $MoS_2$ product can be achieved by decomposing the thiomolybdate in admixture with an inert, preformed particulate diluent, e.g., a preformed, colloidal $ZrO_2$, to produce a matrixed $MoS_2$, i.e., a $MoS_2$-$ZrO_2$ material, having comparable activity and improvement in long-term stability as compared with $MoS_2$ product not so matrixed. In other illustrative embodiments, $MoS_2$-$SiO_2$ mixtures can be made, utilizing a particulate silica of low sodium content, i.e., Ludox AS-40, a du Pont product having an approximately 40% by weight aqueous suspension of approximately 200A° silica powders. A low alkali metal, e.g. sodium, content is desirable since alkali metals have a strong inhibiting effect on methanation over sulfide catalysts.

In other embodiments, the ammonium thiomolybdate salt can be bulk doped with tungsten and vanadium to achieve desirable stability characteristics in the $MoS_2$ catalyst product. Pure $WS_2$, prepared by the thermal decomposition of $(NH_4)_2 WS_4$, possesses both water gas shift and methanation activity, but is less active than its $MoS_2$ analogue. Enhanced stability can be achieved by use of mixed precursor salts prepared by adding $H_2S$ to aqueous ammoniacal solutions containing an ammonium thiomolybdate of the invention, e.g., AOTM, and tungstic acid in controlled ratios. The resulting tungsten doped $MoS_2$ obtained by decomposing the doped, Mo-containing salt of the above formula is $Mo_yW_{1-y}S_2$, where y is generally from about 0.5 to about 0.9. Similarly, replacement of some of the thiomolybdate salt by $V_2O_5$ leads to mixed Mo-V thiosalts, with the resulting vanadium doped product having the empirical composition $Mo_yV_{1-y}S_2$, where y is generally from about 0.5 to about 0.9.

It will be appreciated that it is also within the scope of the invention to support the $MoS_2$ catalyst material on a preformed, porous carrier. For this purpose, various catalyst support and/or dispersion materials, such as alumina, silica, zirconia, thoria, and mixtures thereof, may be considered, with such carriers being employed in a wide variety of concentrations, e.g., from about 10% to about 90% by weight based on the overall weight of catalyst and carrier as in the use of matrixed $MoS_2$ products. Those skilled in the art will appreciate that not all of the commercially available, preformed, porous carrier materials are suitable for application to the $MoS_2$ catalyst system of the invention. The carrier would thus be selected on the overall technical-economic evaluation basis in light of the activity and stability characteristics provided thereby.

In the practice of the process of the invention, thermal decomposition of the thiomolybdate salt in an essentially oxygen-free atmosphere, under controlled conditions, leads to volatization and/or decomposition of the salt to form gaseous products, loss of some S, and of O where x is greater than 0, in volatile form, and formation of solid $MoS_2$ of high surface area in what has been found to be a catalytically active form in accordance with reaction (5) as follows:

$$(NH_4)_2MoS_4 \xrightarrow{\Delta} 2NH_3 \uparrow + H_2S \uparrow + S \uparrow + MoS_2 \qquad (5)$$

The decomposition products of the invention have the approximate composition $MoS_2$, but departures from ideal stoichiometry may occur as a result of (a) incomplete removal of sulfur during catalyst preparation, resulting in S:Mo ratios of greater than two, (b) oxidation of the catalyst surfaces when exposed to moist air, or (c) slow changes that may occur during catalytic use, such as the formation of Mo and $H_2S$ by reaction of $MoS_2$ with hydrogen, or the formation of $MoO_2$ and $H_2S$ by the reaction of $MoS_2$ with water.

Changes in stoichiometry resulting from effects (a) and (b) and falling within the S:Mo range of 1.5–2.5:1 appear to have little influence on catalytic performance. Long-term changes as a result of effect (c) are avoidable by maintaining the $H_2S:H_2$ and $H_2S:H_2O$ ratios in the reactor greater than $10^{-6}:1$ and $10^{-4}:1$, respectively. In general, it appears that, after a very short break-in period, catalytic activity appears quite insensitive to any of the indicated variations from ideal $MoS_2$ stoichiometry.

In addition to the sulfur resistance associated with $MoS_2$ materials, the $MoS_2$ prepared in accordance with the invention has thus been found to have desirable catalytic activity for use in the water gas shift and methanation reactions and for other useful catalytic purposes. In the use of $MoS_2$ catalyst material prepared in accordance with the invention, the product composition has been found to be closer to the thermodynamically predicted equilibrium composition for the water gas shift reaction than for methanation. Short-term screening trials, as reported in the Table above, were generally made without the presence of $H_2S$ in the feed gas stream. In longer term tests to evaluate catalyst lifetime, carried out for several hundred hours with varying levels of $H_2S$ added to the feed, it was found that $H_2S$ led to a mild, reversible poisoning of methanation activity. For practical commercial operations, the feed gas for water gas shift and methanation activities using the sulfur-resistant $MoS_2$ catalyst of the invention can be that generated in a variety of commercial operations, such as (1) various coal gasification processes known in the art, (2) waste disposal systems, e.g., the Union Carbide Corporation PUROX™ System for high temperature incineration and pyrolysis of refuse, and (3) metallurgical operations such as blast furnaces, phosphorous furnaces, metal carbide furnaces and the like. The effluent gases from such operations will normally contain CO and $H_2$, generally within the molecular ratio range of 1:1–1:3, diluents, such as $CO_2$, $N_2$ and $H_2O$, and potential poisons such as $H_2S$. The $MoS_2$ catalysts of the invention operate successfully across a wide range of feed compositions. The tolerable $H_2S$ level can vary from a few ppm to several percent, with the active $MoS_2$ catalyst of the invention having the advantage that the higher levels of $H_2S$ content in the feed gas do not effectively destroy its activity as occurs in the use of other, less sulfur-resistant, methanation catalyst materials. As water is a mild inhibitor, preferred feeds to the catalyst will avoid unnecessary steam addition over that needed from stoichiometric considerations. In practice, the actual feed composition to the catalyst will be determined by various pertinent factors such as the optimum balance between available feed compositions, extent of steam addition required and recycle ratios. The $MoS_2$ catalyst can be employed in any suitable form, as for example in pelleted form in a fixed-bed reactor, with conversion to more attrition-resistant form as hereinabove indicated and with appropriate use of inert, conventional binders as desired, or in finely divided form in a fluidized bed or liquid slurry reactor.

The molybdenum sulfide catalysts prepared under the controlled thermal decomposition conditions of the invention have also been found desirable for use in catalyzed hydrogenation and hydrotreating reactions. For such applications, molybdenum oxides have commonly been converted to the sulfide form prior to or during use, with the molybdenum sulfide being supported in a γ-alumina carrier. Cobalt and/or nickel sulfide is also present as a promoter. Cobalt and/or nickel-promoted $MoS_2$ catalysts prepared by the thiosalt precursor method of the invention have been found to have significantly higher activity than existing commercial products.

The hydrodenitrogenation activity of the $MoS_2$ catalysts of the invention for petroleum feedstock was evaluated in comparative tests utilizing a commercial, alumina-supported, nickel molybdate hydrogenation catalyst, American Cyanamid H-CD, having an apparent bulk density of about 0.85 g/cc. A nickel-promoted $MoS_2$ catalyst was prepared using 357.5 grams of APTM, 144 grams of nickel acetate, $Ni(A_c)_2 \cdot 4H_2O$, 1175 ml of $NH_4OH$ and 500 ml of water. The nickel acetate, ammonium hydroxide and water were combined and split into equal volumes. 178.8 grams of APTM were added to each solution. The mixtures were cooled in an ice bath, and $H_2S$ was bubbled therein until consumption of $H_2S$ and precipitation of N:S, ceased. The precipitate was filtered, washed with denatured alcohol and dried at 80° C. overnight. The combined powders thus obtained were blended in a micro mill and mixed by rolling. The resulting material was pelletized and then reduced in nitrogen by heating rapidly, i.e., at a rate of 20°–30° C./min., to 500° C. at which temperature it was held for about one hour, and then cooled to room temperature in nitrogen, after which air was slowly bled into the chamber. The thus-reduced sample was crushed in a mill, mixed by rolling and pelletized at 5,000 lbs. force using a ½″ diameter die. The pellets were then crushed to 10/20 mesh. The resulting NiS-promoted $MoS_2$ catalyst of the invention had an apparent bulk density of about 1.4 g/cc.

The hydrodenitrogenation catalyst testing was carried out using Union Oil gas oil F-3097, having 1129 ppm of nitrogen and 13,100 ppm of sulfur. A cocurrent gas-liquid, downflow trickle bed having a 1″ inside dia. and 15″ length was employed at a catalyst charge of 100 cc. with 200 cc. of 6×10 mesh fused quartz chips. During test runs of 200 hours, a reaction pressure of 1300 psig was employed at operating temperatures of about 600, 650 and 675° F., with an oil feed flowrate of 100 cc./hr. and a $H_2$ flowrate of 2.04 ft³/hr., with the $H_2$/oil feed rates being 3000 scf/bbl.

After purging with nitrogen and hydrogen, the reactor was pressurized to reaction pressure and set for the desired $H_2$ flowrate. The reactor was heated to 600° F. at the rate of 50° F./hr. At 480° F., the oil feed was started at the desired flowrate. The reaction temperature was maintained at 600° F. for six hours, and the hydrotreated product was sampled. The reaction temperature was then increased to the next desired level, and the product was sampled after steady state had been achieved. Product samples were scrubbed with 4%

NaOH solution to remove dissolved H₂S and NH₃ before analysis for nitrogen and sulfur content.

The nitrogen content of the product was effectively reduced from the 1129 ppm level of the feed material to 212 ppm at about 600° F. and further to 30 ppm at about 650° F. and to 10 ppm at about 675° F. With the commercial catalyst material, on the other hand, the nitrogen level was reduced to 101 ppm at 650° F. and to 36 ppm at 700° F. The nickel-promoted $MoS_2$ of the invention thus exhibited high hydrodenitrogenation activity at advantageously lower operating temperatures than required by the commercial catalyst to achieve desirable results. The catalyst of the invention was also found to have desirable hydrodesulfurization activity. The sulfur content of the products referred to above was found to have been reduced from an initial 13,100 ppm level to 3,058 ppm at about 600° F., to 1,100 ppm at about 650° F., and to 312 ppm at about 675° F.

Other studies have likewise indicated the desirable hydrodesulfurization and hydrodenitrogenation activities of the $MoS_2$ product of the invention, particularly when employed in nickel or cobalt-promoted form. It will be understood that the promoted catalysts can be prepared from the selected thiomolybdate salts by various impregnation and precipitation procedures falling within the scope of the invention as herein disclosed and claimed. As indicated above, it is convenient to form the nickel or cobalt-promoted catalyst by precipitating NiS or CoS in the presence of a selected ammonium thiomolybdate salt, and thereafter thermally treating the mixture to convert the thiomolybdate salt to the highly desirable form of $MoS_2$ produced in the recited process. The nickel or cobalt-promoted catalysts can be prepared with various amounts of nickel or cobalt present for the intended purpose as is known in the art. In particular runs, nickel or cobalt acetates were added to the reaction mixtures in amounts corresponding to a promoter/molybdenum mole ratio of 0.4, this level being selected as being in the range found desirable in the art for maximum hydrosulfurization activity.

While catalysts have been employed in an unsupported, undiluted form in various hydrotreating evaluation applications, it will be appreciated that the commercial aspects of hydrotreating activities will likely require that a support catalyst, e.g., a γ-alumina support, be employed, as in conventional operations, to maintain catalyst costs comparable to existing products in continuous commercial operations.

Since hydrogen is relatively expensive, the amount consumed is another important factor in the economies of commercial hydrotreating operations. Ideally, consumption would be limited to the amount of hydrogen needed to react with the constituents containing heteroatoms, but in practice, it has been found that additional hydrogen is consumed in the hydrogenation of multiple ring aromatic compounds that contain no hetero-atoms. Tests were carried out in which approximately 4 wt. % α-methylnaphthalene was added to the feed for denitrogenation and desulfurization to obtain a measure of the selectivity of the catalysts for denitrogenation and desulfurization as opposed to hydrogenation. Benzothiophene and indole were employed as the sulfur—and nitrogen—containing compounds. The activity of promoted catalysts was greatest for benzothiophene removal, i.e., desulfurization, with indole conversion, i.e., denitrogenation being next in activity and α-methylnaphthelene hydrogenation being of lesser, but significant activity. For indole conversion, promoted $MoS_2$ catalysts prepared in accordance with the process of the present invention from the indicated thiosalt was more active than the above-mentioned H-CD catalyst. The hydrogenation of α-methylnaphthalene by means of the $MoS_2$ catalyst of the invention, using a nickel-promoted catalyst and, at a lower activity level, unpromoted $MoS_2$ catalyst, is an illustrative embodiment of the catalyst properties of the $MoS_2$ products of the invention for hydrogenation reactions.

The improved hydrodesulfurization and hydrodenitrogenation of liquid fuels will be needed when it becomes necessary to process lower grade petroleum feedstocks and the alternate fuel sources, such as liquified coal, shale oil, tar sands, and the like, that are under consideration as replacements for petroleum. The $MoS_2$ catalysts prepared in accordance with the invention are of significance, therefore, in a number of highly important applications related to the ever-growing search for new and improved technologies for meeting the energy and chemical feedstock requirements of industrial societies.

What is claimed is:

1. A process for the production of improved, sulfur resistant catalysts comprising thermally decomposing an ammonium salt of molybdenum-sulfur cluster anions or an ammonium thiomolybdate salt having the formula $(NH_4)_2[MoO_xS_{4-x}]$, where x is from about 0.8 to about 2.2, at a decomposition temperature of from about 300° C. to about 800° C., said salt being heated to the decomposition temperature rapidly at a rate in excess of about 15° C./min. in an essentially oxygen-free atmosphere, said salt decomposing at said temperature to form a high surface area, bulk molybdenum disulfide, $MoS_2$, having desirable properties for use as a catalyst for water gas shift and methanation reactions and for catalyzed hydrogenation or hydrotreating reactions.

2. The process of claim 1 in which said salt is decomposed at a temperature of from about 400° C. to about 500° C.

3. The process of claim 1 in which said salt is heated to the decomposition temperature at a rate on the order of about 20° C./min. to about 30° C./min.

4. The process of claim 1 in which the molybdenum disulfide has a surface area of from about 50 to about 150 m²/gm.

5. The process of claim 1 in which said salt is an ammonium thiomolybdate salt in which x is 2.

6. The process of claim 1 in which said salt is the ammonium salt of molybdenum-sulfur cluster anions.

7. The process of claim 1 in which said essentially oxygen-free atmosphere comprises a nitrogen or argon atmosphere.

8. The process of claim 1 in which the heating and decomposition of the salt occurs under vacuum.

9. The process of claim 5 in which said salt is decomposed at a temperature of from about 400° C. to about 500° C., said salt being heated at a rate of from about 20° to about 30° C./min.

10. The process of claim 5 in which said molybdenum disulfide has a surface area of from about 50 to about 150 m²/gm.

11. The process of claim 6 in which said thiomolybdate salt is $(NH_4)_2Mo_3S_{13}\cdot xH_2O$.

12. The process of claim 6 in which said salt is decomposed at a temperature of from about 400° C. to about 500° C., said salt being heated to the decomposition temperature at a rate on the order of from about 10° to about 30° C./min.

13. The process of claim 6 in which said molybdenum disulfide has a surface area of from about 50 to about 150 m²/gm.

14. The process of claim 7 in which said essentially oxygen-free atmosphere contains up to about 10% by volume of hydrogen.

15. A process for the production of an improved, sulfur resistant catalyst comprising thermally decomposing ammonium thiomolybdate at a decomposition temperature of from about 300° C. to about 800° C., said salt being heated to the decomposition temperature rapidly at a rate in excess of about 15° C./min. in an essentially oxygen-free atmosphere, said salt decomposing at said temperature to form a high surface area, bulk molybdenum disulfide, $MoS_2$, having desirable properties for use as a catalyst for water gas shift and methanation reactions and for catalyzed hydrogenation or hydrotreating reactions.

16. The process of claim 15 in which said salt is decomposed at a temperature of from about 400° C. to about 500° C.

17. The process of claim 16 in which said salt is heated to the decomposition temperature at a rate on the order of about 20° to about 30° C./min.

18. An improved, sulfur resistant catalyst produced by the process comprising thermally decomposing an ammonium salt of molybdenum-sulfur cluster anions or an ammonium thiomolybdate salt having the formula $(NH_4)_2 [MoO_xS_{4-x}]$, where x is from about 0.8 to about 2,2, at a decomposition temperature of from about 300° C. to about 800° C., said salt being heated to the decomposition temperature rapidly at a rate in excess of about 15° C./min. in an essentially oxygen-free atmosphere, said salt decomposing at said temperature to form a high surface area, bulk molybdenum disulfide, $MoS_2$, having desirable properties for use as a catalyst for water gas shift and methanation reactions and/or catalyzed hydrogenation or hydrotreating reactions.

19. The catalyst of claim 18 in which said salt is decomposed at a temperature of from about 400° C. to about 500° C., said salt being heated to the decomposition temperature at a rate of from about 20° C./min. to about 30° C./min., said product molybdenum disulfide having a surface area of from about 50 to about 150 m²/gm.

20. The catalyst of claim 17 in which said salt is an ammonium thiomolybdate salt in which x is 2.

21. The catalyst of claim 19 in which said salt is the ammonium salt of a molybdenum-sulfur cluster anion.

22. The catalyst of claim 21 in which said thiomolybdate salt is $(NH_4)_2Mo_3S_{13} \cdot xH_2O$.

23. An improved, sulfur resistant catalyst produced by the process comprising thermally decomposing ammonium thiomolybdate at a decomposition temperature of from about 300° C. to about 800° C., said salt being heated to the decomposition temperature rapidly at a rate in excess of about 15° C./min. in an essentially oxygen-free atmosphere, said salt decomposing at said temperature to form a high surface area, bulk molybdenum disulfide, $MoS_2$, having desirable properties for use as a catalyst for water gas shift and methanation reactions and/or catalyzed hydrogenation or hydrotreating reactions.

24. The catalyst of claim 23 in which said thiomolybdate is decomposed at a temperature of from about 400° C. to about 500° C., said salt being heated to the decomposition temperature at the rate of from about 20° to about 30° C./min.

* * * * *

UNITED STATES PATENT AND TRADEMARK OFFICE
CERTIFICATE OF CORRECTION

PATENT NO. : 4,243,554
DATED : January 6, 1981
INVENTOR(S) : Naumann, et al.

It is certified that error appears in the above—identified patent and that said Letters Patent is hereby corrected as shown below:

The table at the top of column 7 and 8 should read as follows:

TABLE

| | Catalytic Performance | | | |
|---|---|---|---|---|
| | Initial(a) Performance | | After Overnight Operation | |
| Catalyst Type | % CO to Hydrocarbons | % CO Conv. | % CO to Hydrocarbons | % CO Conv. |
| 1. Commercial $MoS_2$ | nil | nil | -- | -- |
| 2. Sulfided Ammonium Paramolybdate (APM) | 36 | 63 | -- | -- |
| 3. Sulfided $MoO_3/Al_2O_3$ | 48 | 82 | -- | -- |
| 4. Sulfided Climax $Mo-MoO_2$(b) | 30 | 54 | -- | -- |
| 5. $MoS_2$ from Ammonium Thiomolybdate (ATM) | 75 | 99 | 63 | 90 |
| 6. $MoS_2$ from Ammonium Oxythiomolybdate (AOTM) | 81 | >99 | 81 | >99 |
| 7. $MoS_2$ from the Ammonium salt of Molybdenum-Sulfur Cluster Anion (APTM) | 87 | >99 | 82 | >99 |

(a) 400°C outlet; 400 psig; $CO:H_2$ = 1:3; SV = 3000 $hr^{-1}$
(b) obtained from American Metals Climax Co.

UNITED STATES PATENT AND TRADEMARK OFFICE
CERTIFICATE OF CORRECTION

PATENT NO. : 4,243,554

DATED : January 6, 1981

INVENTOR(S) : Naumann, et al.

It is certified that error appears in the above—identified patent and that said Letters Patent is hereby corrected as shown below:

Column 3, line 26 to 27, "molybdenumsulfur" should read --molybdenum-sulfur --.

Column 14, line 11, claim 20 dependence on "17" should read on -- 19 --.

Signed and Sealed this

Fourteenth Day of July 1981

[SEAL]

Attest:

Attesting Officer

GERALD J. MOSSINGHOFF

Commissioner of Patents and Trademarks